US005725553A

United States Patent [19]
Moenning

[11] Patent Number: 5,725,553
[45] Date of Patent: Mar. 10, 1998

[54] APPARATUS AND METHOD FOR PROTECTING A PORT SITE OPENING IN THE WALL OF A BODY CAVITY

[76] Inventor: Stephen P. Moenning, 124 Hibiscus, Punta Gorda, Fla. 33950

[21] Appl. No.: 656,430

[22] Filed: May 30, 1996

Related U.S. Application Data

[63] Continuation-in-part of Ser. No. 608,644, Feb. 29, 1996.

[51] Int. Cl.[6] ........................................ A61B 17/08
[52] U.S. Cl. ............................... 606/213; 606/214
[58] Field of Search ......................... 606/213, 214, 606/215, 191, 192, 193, 197; 604/164, 165, 171, 174, 268, 104, 105

[56] References Cited

U.S. PATENT DOCUMENTS

| 5,290,249 | 3/1994 | Foster et al. | 604/174 |
|---|---|---|---|
| 5,330,497 | 7/1994 | Freitas et al. | 606/185 |
| 5,366,446 | 11/1994 | Tal et al. | 604/110 |
| 5,368,545 | 11/1994 | Schaller et al. | 600/37 |
| 5,370,647 | 12/1994 | Graber et al. | 606/127 |
| 5,391,156 | 2/1995 | Hildwein et al. | 604/174 |

FOREIGN PATENT DOCUMENTS

| 0 542428 A | 5/1993 | European Pat. Off. | A61B 17/34 |
|---|---|---|---|
| WO 95/24864 | 9/1995 | WIPO | A61B 17/04 |

*Primary Examiner*—Michael Buiz
*Assistant Examiner*—Tina T. D. Pham
*Attorney, Agent, or Firm*—Maginot, Addison & Moore

[57] ABSTRACT

A medical apparatus includes a trocar assembly including a cannula and a trocar. The medical apparatus also includes a sleeve having a number of sealing members extending therefrom, and a passageway extending therethrough, with the trocar assembly being positioned within the passageway of the sleeve. The medical apparatus further includes a sealing member which defines a flexible, gas impervious bag having an interior void and a charge of beads confined within the interior void. The medical apparatus still further includes a lock member, and a sealing member having a biologically active compound disposed thereon. The sleeve is positionable within an opening defined in a wall of a body cavity. Moreover, the sealing members are movable between (1) a first orientation in which the sealing members are positioned to facilitate advancement of the sleeve into the opening, and (2) a second orientation in which the sealing members are positioned to prevent fluid communication between an area inside of the body cavity and an area outside of the body cavity through a space defined between the opening of the body cavity and the sleeve. A medical procedure which uses the medical apparatus is also disclosed.

18 Claims, 16 Drawing Sheets

APPARATUS AND METHOD FOR PROTECTING A PORT SITE OPENING IN THE WALL OF A BODY CAVITY

This application is a continuation-in-part of co-pending U.S. application Ser. No. 08/608,644, filed Feb. 29, 1996.

BACKGROUND OF THE INVENTION

The present invention generally relates to an apparatus and method for protecting a port site opening in the wall of a body cavity. The present invention particularly relates to an apparatus and method for protecting a port site opening in the wall of a body cavity which is used with a trocar assembly.

Minimally invasive surgical techniques, such as laparoscopic surgery, typically include the use of a trocar to create a small hole or port in a wall of a body cavity so as to gain access to the body cavity. Surgery performed by using these techniques is generally associated with lower postoperative morbidity, shorter postoperative stay, less postoperative pain, decreased cost, and quicker recovery as compared to "open" or conventional surgical techniques. Because of the aforementioned advantages, these minimally invasive techniques are being applied to an increasing variety of all surgical procedures. For example, laparoscopic procedures for the resection of malignancies have emerged. In particular, laparoscopic colectomy for carcinoma of the colon has been developed, and it has been reported that the initial results of these procedures have advantages over operations performed in the traditional open manner. Moreover, it is hoped that the long term results of these procedures will be comparable, or better than, those performed in the traditional open manner.

However, the field of laparoscopic surgery for cancer has been delayed in its development because of the major concern regarding the implantation of tumor cells in the port site wound. Minimally invasive surgical techniques for treating cancer require the removal of a malignant neoplasm through the small incision or port site created by a trocar. These procedures require the dragging of tumor tissue through the port site which creates a risk of implanting tumor cells in the walls of the wound forming the extraction site. An additional concern is that tumor cells exfoliated during the procedure will come into contact with, and contaminate, the port site wound. This contamination can occur as a result of the exfoliated tumor cells being in fluid communication with the port site wound. Regardless of how these cells contaminate the wound, once implanted therein, viable tumor cells can cause a subcutaneous metastases or "port/extraction site recurrence" after the resection of malignant tissue. In fact, numerous port site recurrences have been documented in the medical literature heretofore; and subcutaneous metastases after laparoscopic resection of malignant tissue has been described as a potentially serious complication of laparoscopic cancer surgery. These "port/ extraction site recurrences" have delayed the advancement of laparoscopic cancer surgery.

Furthermore, laparoscopic surgery performed for general surgery, gynecological surgery, urological surgery, or any other intra-abdominal infection is associated with a small but real incidence of port site wound infection. The infecting bacteria causing these illnesses can contaminate the port site wound by the same mechanism as discussed above with reference to tumor cell contamination, and these infections can increase a patients morbidity and consequently the length of a patient's hospital stay, thereby considerably increasing their hospital bill.

Therefore, in light of the above discussion, it is apparent that an apparatus for preventing port site tumor implantation and reducing the incidence of port site infection, is desirable. The present invention provides such an apparatus in the form of a protective trocar sleeve. One advantage the present invention has over the prior art is that it can be retrofit to existing trocar assembly technology. Moreover, once attached, the described invention adds only a minimal amount of bulk to the diameter of the trocar assembly.

In use, the present invention protects the port site from infection or tumor cell implantation thereby lowering the morbidity and mortality of a wide variety of minimally invasive surgical techniques. The present invention allows the field of laparoscopic surgery to be safely applied to all forms of cancer surgery while minimizing "port site recurrences." The present invention also allows the field of laparoscopic surgery to be safely applied to all forms of laparoscopy while minimizing port site infections.

SUMMARY OF THE INVENTION

In accordance with one embodiment of the present invention, there is provided a medical apparatus which includes a trocar assembly including a cannula and a trocar. The medical apparatus includes a sleeve having a number of sealing members extending therefrom and a passageway extending therethrough, said trocar assembly being positioned within said passageway of said sleeve. The medical apparatus further includes a lock member which has hole defined therein, said sleeve extending through the hole.

Pursuant to another embodiment of the present invention, there is provided a medical apparatus which includes a trocar assembly having a cannula and a trocar. The medical apparatus further includes a sleeve having a number of sealing members extending therefrom and a passageway extending therethrough, said trocar assembly being positioned within said passageway of said sleeve, and wherein (1) said number of sealing members define a fluid impervious bag, (2) said bag has an interior void, and (3) a plurality of beads are confined within said interior void.

According to yet another embodiment of the present invention, there is provided a medical apparatus which includes a trocar assembly including a cannula and a trocar. The medical apparatus further includes a sleeve having a number of sealing members extending therefrom and a passageway extending therethrough, said trocar assembly being positioned within said passageway of said sleeve. In addition, the medical apparatus includes an antibiotic, a cytotoxic agent, or a compound which inhibits tumor cell adherence to a membrane disposed upon said sealing members.

Pursuant to still another embodiment of the present invention, there is provided a medical procedure which includes the following steps (1) creating an opening in a wall of a body cavity, (2) advancing a medical apparatus through the opening and into the body cavity, the medical apparatus including (a) a sleeve having a number of sealing members connected thereto and a passageway extending therethrough, and (b) a trocar assembly positioned within the passageway of the sleeve, the trocar assembly including a cannula and a trocar, (3) positioning the sealing members to contact an interior surface of the body cavity, (4) providing a lock member having a hole extending therethrough; and (5) positioning the lock member such that the sleeve extends through the hole.

It is therefore an object of the present invention to provide a new and useful medical apparatus.

It is another object of the present invention to provide an improved medical apparatus.

It is still another object of the present invention to provide a new and useful medical apparatus for protecting a port site wound from tumor cell implantation or contamination with an infectious agent.

It is another object of the present invention to provide an improved medical apparatus for protecting a port site wound from tumor cell implantation or contamination with an infectious agent.

It is moreover an object of the present invention to provide a new and useful medical procedure for performing minimally invasive surgery.

It is still another object of the present invention to provide an improved medical procedure for performing minimally invasive surgery.

It is also an object of the present invention to provide a medical apparatus for protecting a port site wound which can be retrofit to existing trocar assembly technology.

It is still another object of the present invention to provide a medical apparatus for protecting a port site wound which adds only a minimal amount of bulk to the diameter of a trocar assembly.

It is yet another object of the present invention to provide a medical apparatus which protects against the loss of the pneumoperitoneum.

It is still another object of the present invention to provide a medical apparatus which is securely positioned in the port site wound.

The above and other objects, features, and advantages of the present invention will become apparent from the following description and attached drawings.

DETAILED DESCRIPTION OF THE PREFERRED EMBODIMENT

Figure 1:
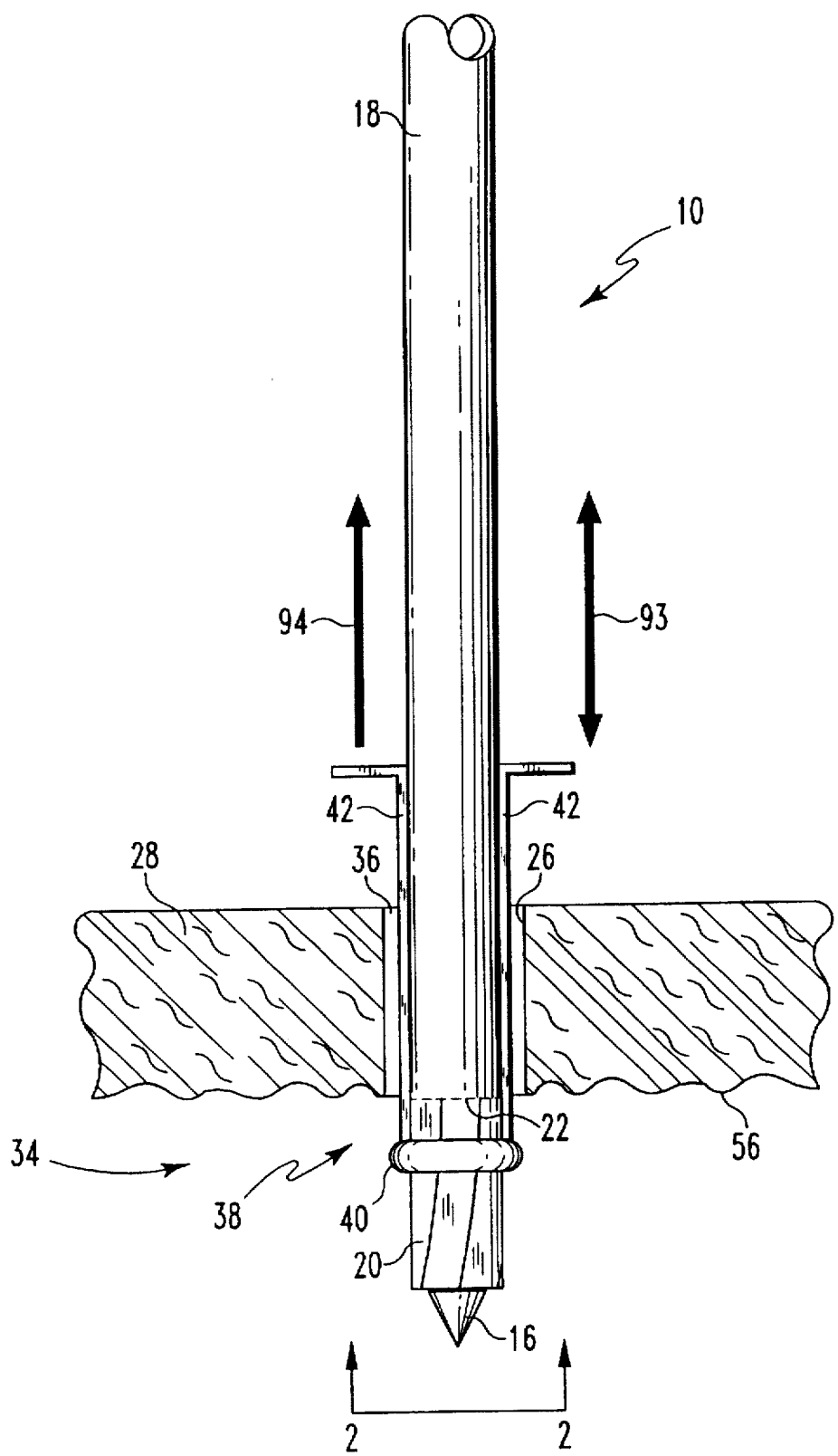
FIG. 1 is a fragmentary side elevational view of a medical apparatus inserted through a body cavity wall which incorporates the features of the present invention therein, with the body cavity wall shown in cross-section for clarity of description.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Figure 4:
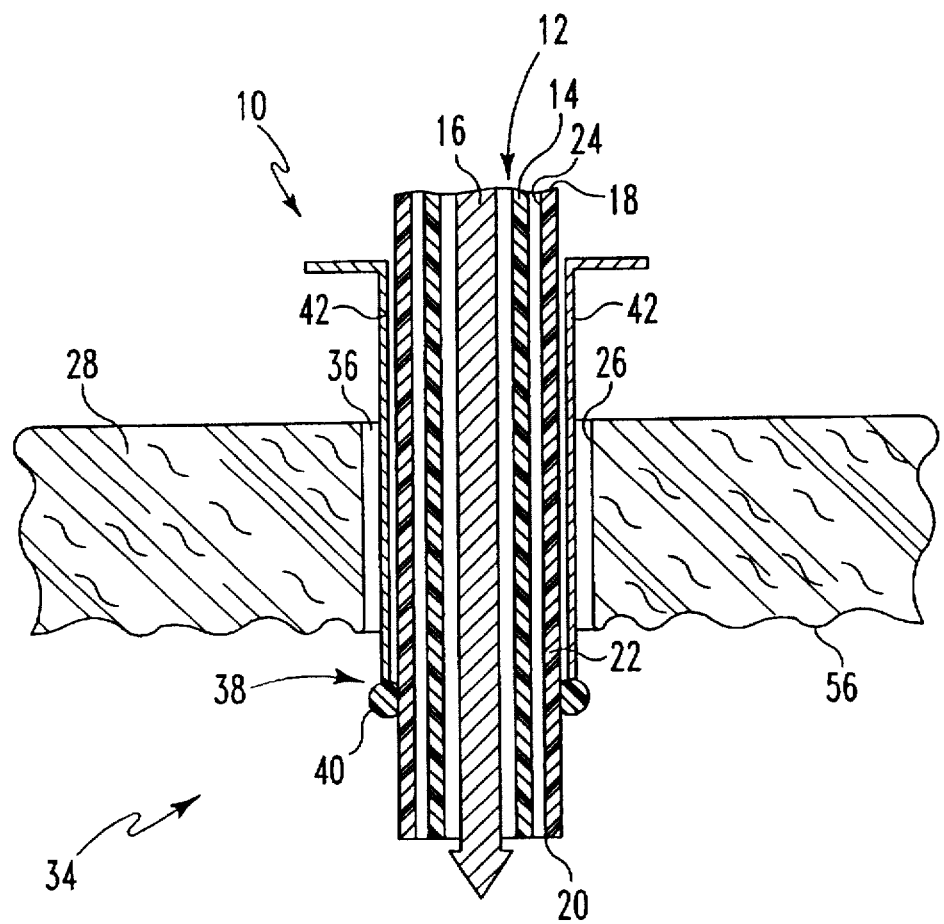
FIG. 4. is an enlarged cross sectional view of the medical apparatus of FIG. 1, with the guide member shown in a first position and the sealing members shown in a first orientation.
Figure 5:
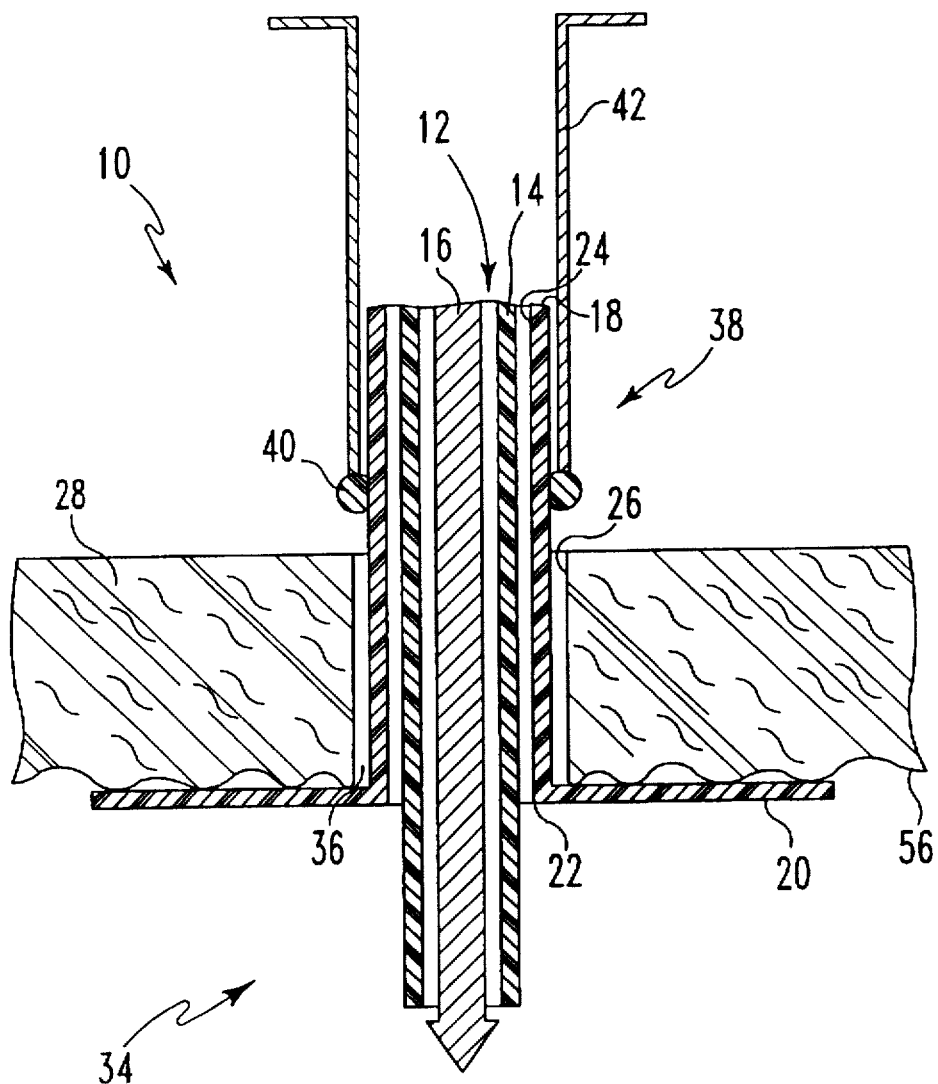
FIG. 5 is an enlarged cross sectional view of the medical apparatus of FIG. 1, with the guide member shown in a second position and the sealing members shown in a second orientation.

Referring to FIGS. 1, 4 and 5 there is shown a medical apparatus 10 of the present invention advanced through an opening 26 in a wall 28 of a body cavity 34. The medical apparatus 10 includes a sleeve 18 having a passageway 24 extending therethrough. The sleeve 18 includes a number of sealing members 20. The medical apparatus further includes an actuator 38 and a trocar assembly 12. The actuator 38 includes a guide member 40 and handles 42. The sealing members 20 extend from a distal end 22 of sleeve 18. The trocar assembly 12 includes a cannula 14 and a trocar 16 positioned within passageway 24 of the sleeve 18.

Figure 2:
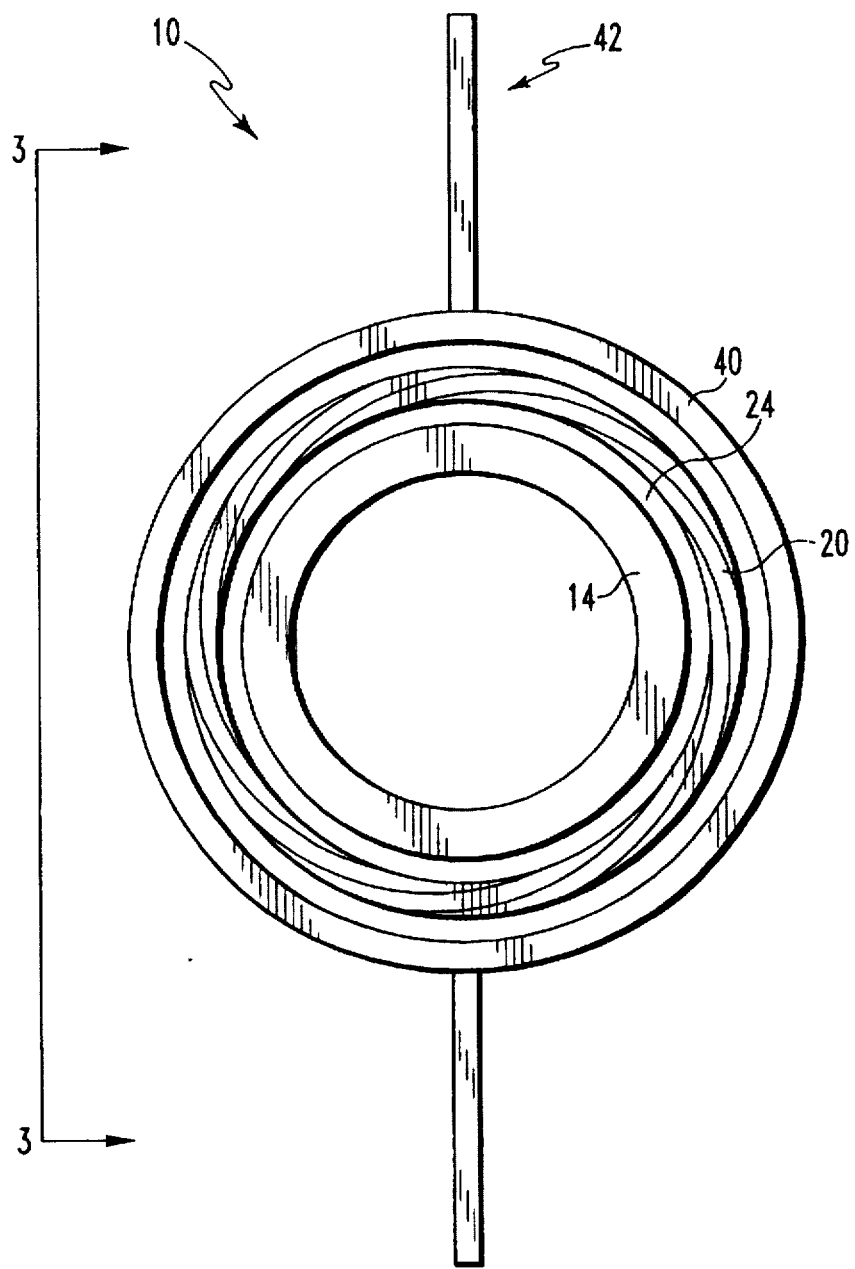
FIG. 2 is an enlarged end elevational view of the medical apparatus taken along line 2—2 of FIG. 1, with the trocar and body cavity wall shown removed for clarity of description.
Figure 3:
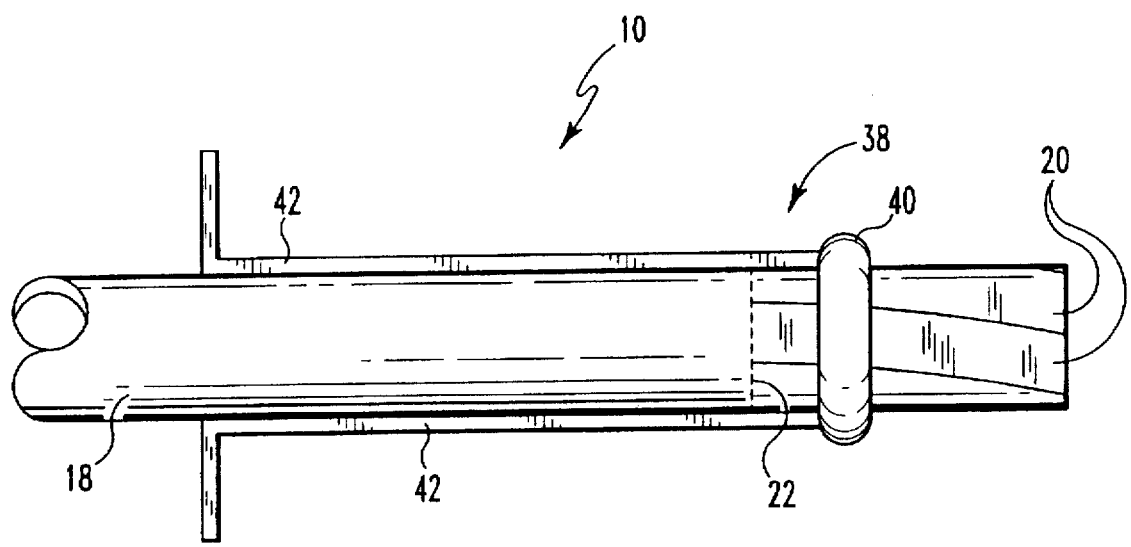
FIG. 3. is a reduced fragmentary side elevational view of the medical apparatus taken along line 3—3 of FIG. 2.

As illustrated in FIG. 2, cannula 14, sealing members 20, and guide member 40 are all respectively nested within each other in a substantially concentric relationship (a portion of handles 42 is also shown extending above guide member 40). Cannula 14 is slidably fit into passageway 24 of sleeve 18 so as to allow its movement relative to sleeve 18. It should also be understood that cannula 14 and sleeve 18 are fit in such a way as to form a substantially gas tight junction so that substantially no gas leakage occurs through this junction during insufflation of the body cavity 34. The aforementioned gas tight junction may be formed using rubber gaskets or o-rings.

Figure 6:
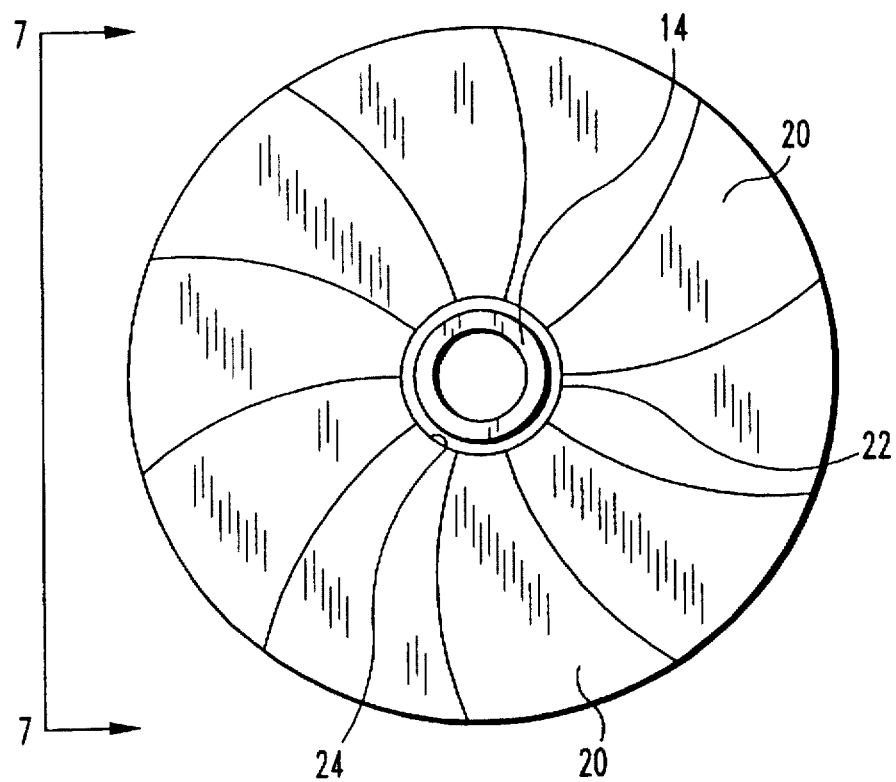
FIG. 6 is a view similar to FIG. 2, however the medical apparatus is shown reduced, and the sealing members are shown in the second orientation.
Figure 7:
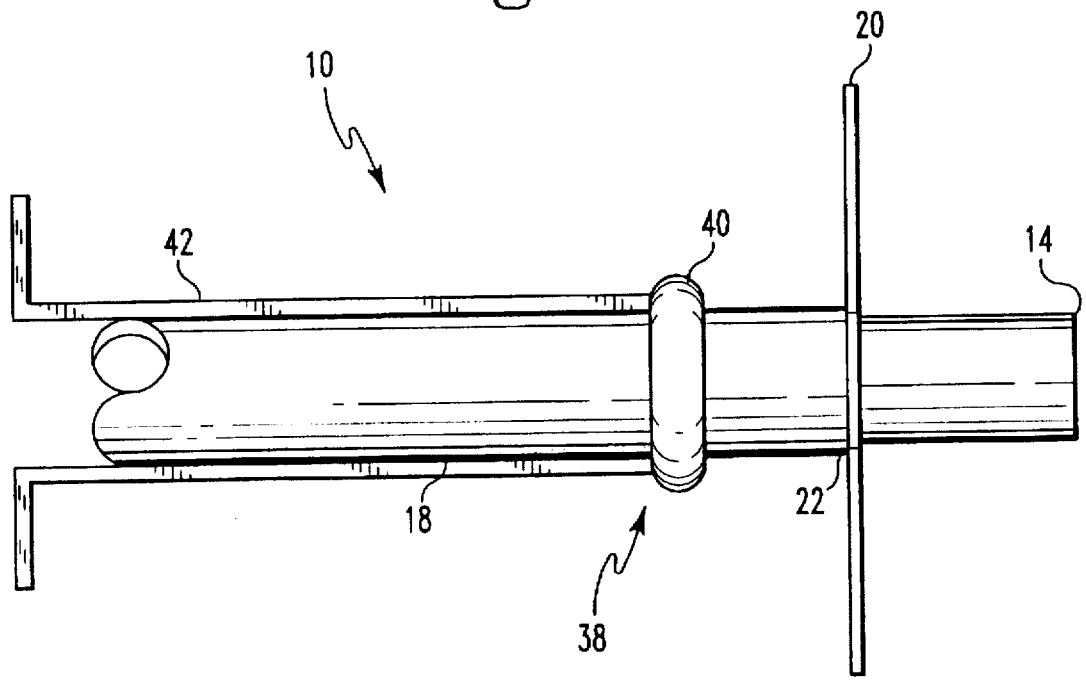
FIG. 7 is a fragmentary side elevational view of the medical apparatus taken along line 7—7 of FIG. 6.

Guide member 40 is slidably mounted onto sleeve 18 so it can be moved between a first position as shown in FIG. 4 and a second position as shown in FIG. 5. The double headed arrow 93 of FIG. 1 shows the direction of movement of guide member 40. Specifically, FIGS. 1–4 show guide member 40 placed in the first position, whereas FIGS. 5 and 7 show guide member 40 placed in the second position. As illustrated in FIGS. 1, 3, 5 and 7, the position of guide member 40 controls the movement of sealing members 20 between a first orientation and a second orientation. The sealing members 20 are positioned in the first orientation when the sealing members 20 are positioned in a substantially parallel relationship with passageway 24 of sleeve 18, as shown in FIGS. 1–4. The sealing members 20 are positioned in the second orientation when the sealing members 20 are positioned in a substantially orthogonal relationship with passageway 24 of sleeve 18 as shown in FIGS. 5–7. Moreover, as depicted in FIG. 6, when sealing members 20 are in the second orientation they extend from the distal end 22 of sleeve 18 (not shown in FIG. 6) so as to overlap one another, thereby completely surrounding passageway 24 of sleeve 18.

FIG. 6 shows sealing members 20 extending to form an annular flange. However, it should be appreciated that the present invention is not limited to the geometric shape formed by the extending sealing members. For example, other geometric shapes are contemplated, such as square or oval shaped configurations. Moreover, a single sealing member extending from a distal end of a sleeve, or a number of non-overlapping sealing members spaced around a distal end of a sleeve are also contemplated. Furthermore, sealing members having perforations thereon which can be torn and separated prior to positioning in contact with the interior surface of a body cavity wall are also contemplated.

Sleeve 18 and guide member 40 can be made from any plastic material which is conventionally used in the medical device arts. Such material would be compatible with insertion into a body cavity. It should also be noted that the guide member used in the present invention can be manufactured to a size which only adds a minimal amount of bulk to the diameter of a trocar assembly. By doing so, trauma to the body cavity wall upon insertion of the medical apparatus of the present invention will be reduced.

Sleeve 18 and sealing members 20 are formed such that when no force is applied to sealing members 20 they spontaneously assume their second orientation (see FIGS. 5–7). Moreover, sealing members 20 are flexibly attached to distal end 22 such that when force is applied (i.e. the force applied by sliding guide member 40 over the sealing members 20) the sealing members 20 assume their first orientation (see FIGS. 1–4).

Handles 42 can be made of any material having the appropriate beam strength to move guide member 40 from the first position to the second position.

When performing a medical procedure with medical apparatus 10, such as a laparoscopic surgery, guide member 40 is placed into the first position (see FIGS. 1–4) so that sealing members are maintained in their first orientation (see FIGS. 1–4). Trocar 16 of medical apparatus 10 then contacts with and is advanced through wall 28 of a body cavity 34 to create an opening 26. Preferably, sleeve 18 and trocar 16 are simultaneously advanced through the opening 26 and into body cavity 34. It should be appreciated that tabs may be positioned on the sleeve 18 to prevent handles 42 and guide member 40 from being forced in the direction of arrow 94 (and therefore toward their second position (see FIGS. 5 and 7)) during the advancement of medical apparatus 10 through wall 28. It should also be appreciated that maintaining guide member 40 in its first position, and therefore sealing members 20 in their first orientation, facilitates the advancement of sleeve 18 through opening 26 and into body cavity 34.

Once distal end 22 of medical apparatus 10 enters into body cavity 34 through opening 26, handles 42 are moved away from opening 26 in the direction of arrow 94 (see FIG. 1) so as to slide guide member 40 to the second position (see FIGS. 5 and 7), thereby allowing sealing members 20 to assume their second orientation. Once sealing members 20 have assumed their second orientation they are positioned to contact the interior surface 56 of the body cavity wall 28 so as to prevent fluid communication between an area inside of the body cavity and an area outside of the body cavity through the space 36 defined between the opening 26 and the sleeve 18.

It should be understood that a non-perforating ridge (not shown) or a number of non-perforating "flange teeth" (not shown) extending from the surface of the sealing members and contacting the interior surface of the body cavity wall is also contemplated. Such a ridge or "flange teeth" will also contact the interior surface of the body cavity wall and assist in preventing fluid communication between the area inside of the body cavity and the area outside of the body cavity through the space defined between the opening and the sleeve. The aforementioned ridge or "flange teeth" will also keep the sealing members stationary relative to the interior surface of the body cavity during manipulations of the cannula.

Once the medical procedure is completed, handles 42 are moved toward opening 26 in a direction opposite to arrow 94 so as to slide guide member 40 to the first position (see FIGS. 1–4). The movement of guide member 40 to the first position forces sealing members 20 to assume their first orientation (see FIGS. 1–4), thereby facilitating the removal of medical apparatus 10 from opening 26.

Figure 8:
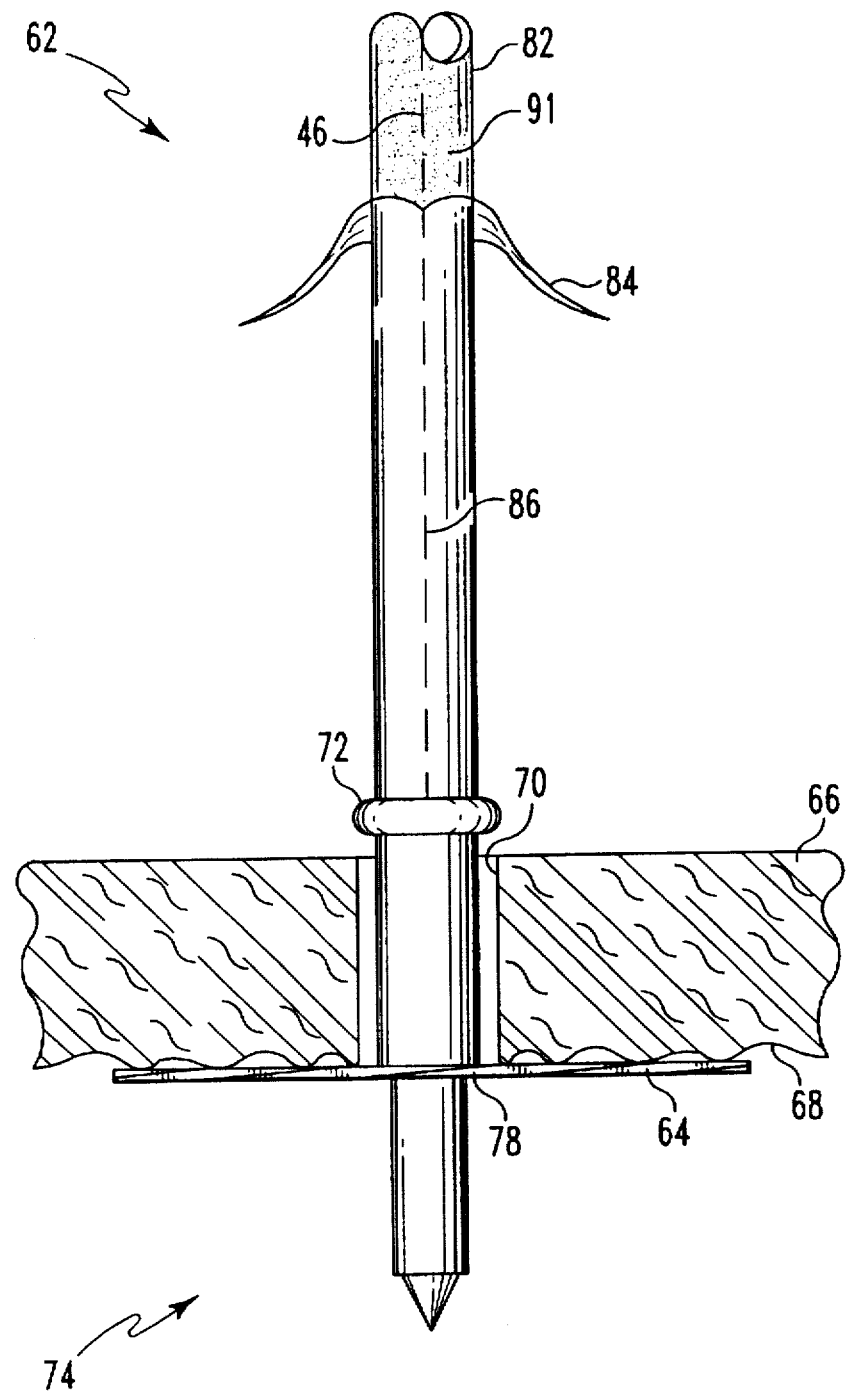
FIG. 8 is a fragmentary side elevational view of a medical apparatus similar to the one shown in FIG. 1, but this medical apparatus includes a strippable liner thereon (the handles are shown removed for clarity of description)

Now referring to FIG. 8, there is shown a medical apparatus 62 similar to the medical apparatus 10 shown in FIG. 1. Medical apparatus 62 is shown advanced through an opening 70 in a wall 66 of a body cavity 74. The medical apparatus 62 includes a sleeve 82 having a plurality of perforations 86 defined in its proximal end portion and an adhesive material disposed on its outer surface 91. The sleeve 82 includes a number of sealing members 64 positioned in a second orientation extending from distal end 78. The medical apparatus 62 further includes a guide member 72 positioned in the second position. Medical apparatus 62 also includes a strippable liner 84, surrounding and in contact with, the adhesive material disposed on outer surface 91. The strippable liner has perforations 86 formed thereon.

Figure 9:
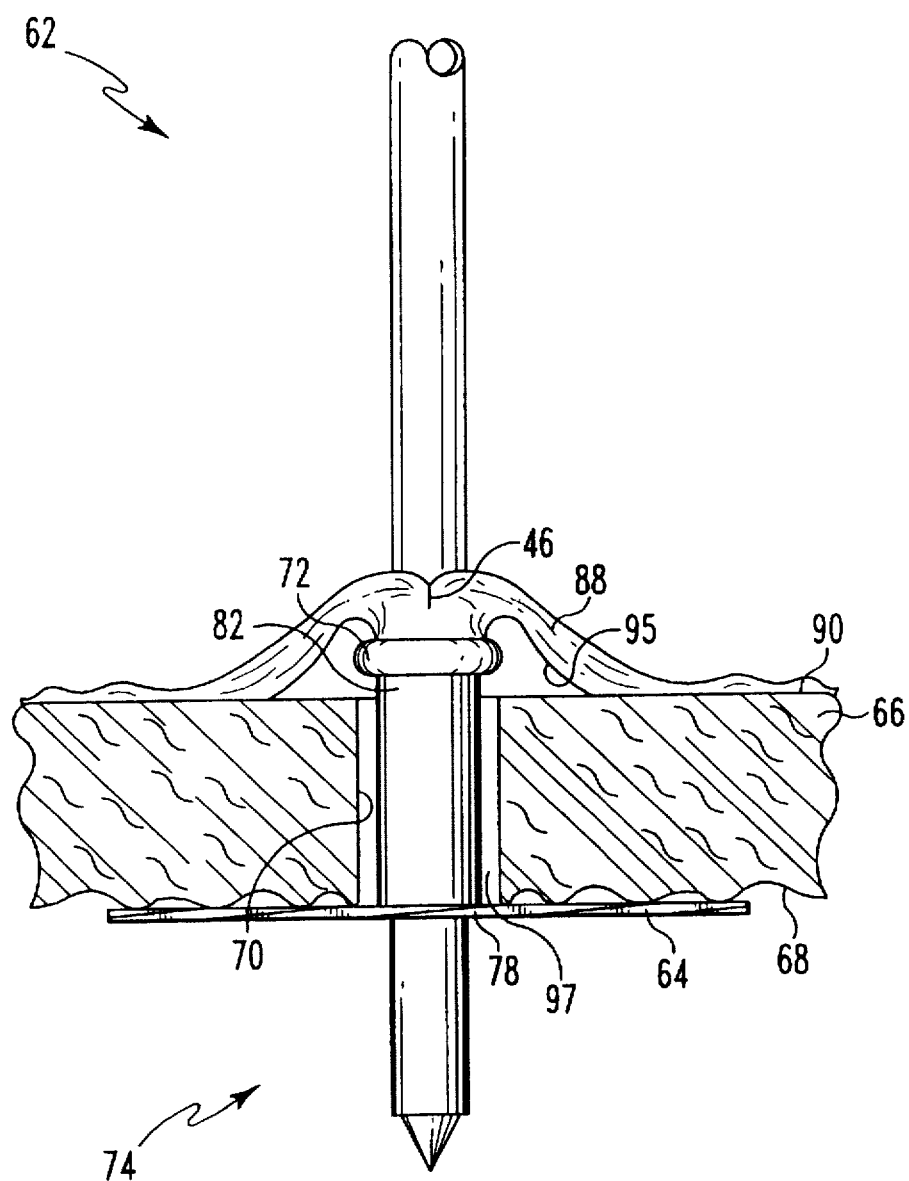
FIG. 9 is a fragmentary side elevational view of the medical apparatus shown in FIG. 8, with the strippable liner peeled off, and the sleeve peeled down and attached to an exterior surface of a body cavity wall.

Medical apparatus 62 is used in the same manner as described above with reference to medical device 10. However, once the sealing members are positioned in contact with an interior surface 68 of body cavity wall 66, strippable liner 84 is torn along perforations 86 to expose the adhesive material disposed on the outer surface 91 of sleeve 82. As shown in FIG. 9, sleeve 82 is then torn along perforations 86 down to guide member 72 to form a number of elongated strips 88 having a first surface 95 with the adhesive disposed thereon. It is also contemplated that sleeve 82 may be formed from a material having the physical property of molecular orientation whereby a tear in the material runs readily only in a longitudinal direction along the length of sleeve 82. A sleeve formed from such a material will eliminate the need for the above described perforations. Once the elongated strips 88 are formed, a first surface 95 of each strip 88 is attached to an exterior surface 90 of body cavity wall 66 with the adhesive.

An important aspect of using elongated strips 88 in the above described manner is that they cooperate with sealing members 64 to stabilize the position of medical apparatus 62 in opening 70. The attachment of elongated strips 88 to the exterior surface 90 of body cavity wall 66 also keeps sealing members 64 in contact with interior surface 68. This ensures that no fluid communication exists between an area inside of the body cavity 74 and an area outside the body cavity through the space 97 defined between the opening 70 and the sleeve 82.

Figure 10:
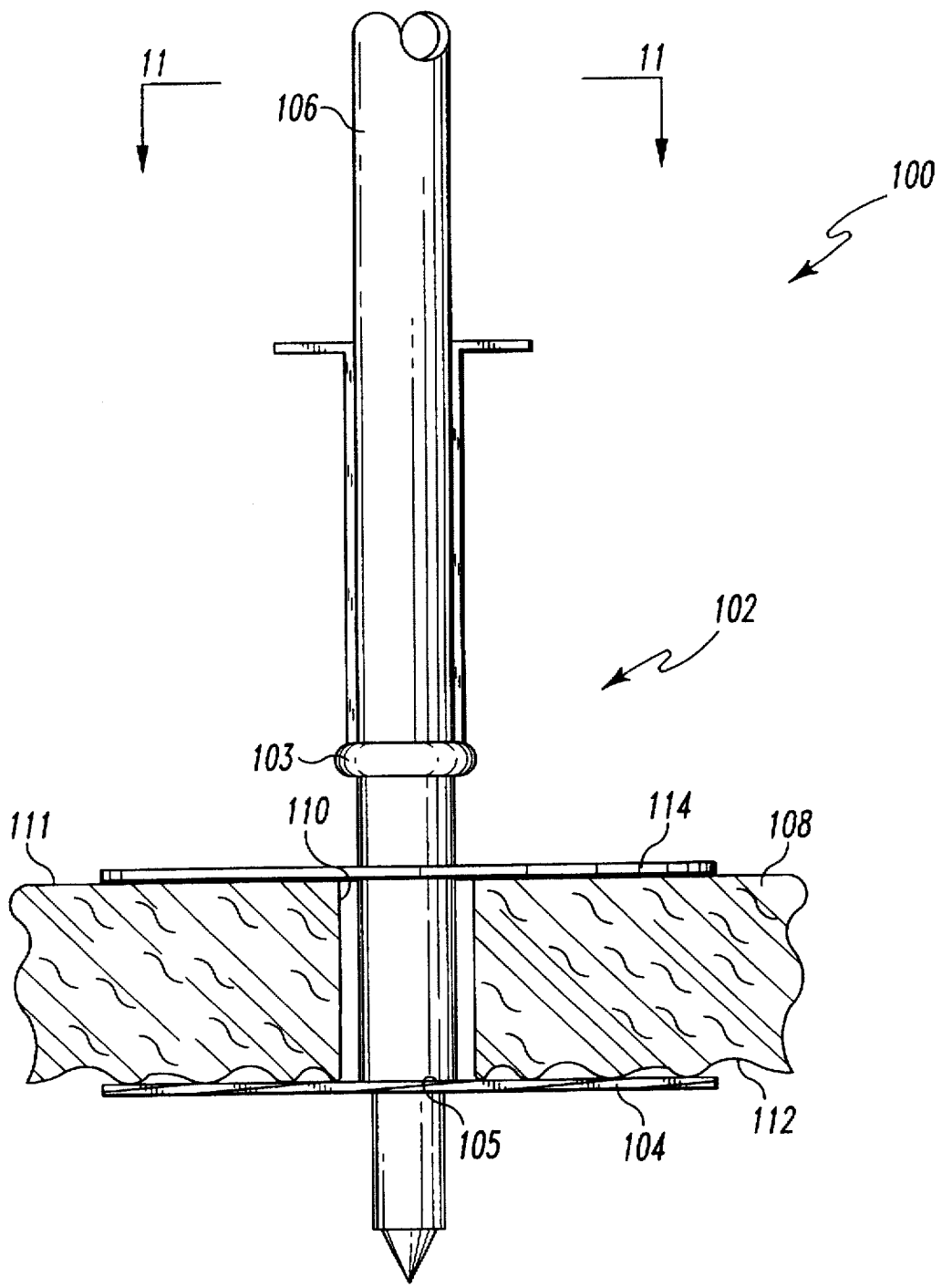
FIG. 10 is a fragmentary side elevational view of a medical apparatus similar to the one shown in FIG. 1, but this apparatus includes a lock member.

Now referring to FIG. 10, there is shown a medical apparatus 100 similar to the medical apparatus 10 shown in FIG. 1. Medical apparatus 100 is shown advanced through an opening 110 in a wall 108 of a body cavity. Medical apparatus 100 includes a sleeve 106 having a number of sealing members 104 positioned in the second orientation extending from distal end 105 of sleeve 106, and in contact with interior surface 112 of body wall 108. The medical apparatus 100 further includes an actuator 102 with a guide member 103 located in the second position. Medical apparatus 100 also includes a lock member 114 positioned in contact with sleeve 106 and exterior surface 111 of body cavity wall 108.

Figure 11:
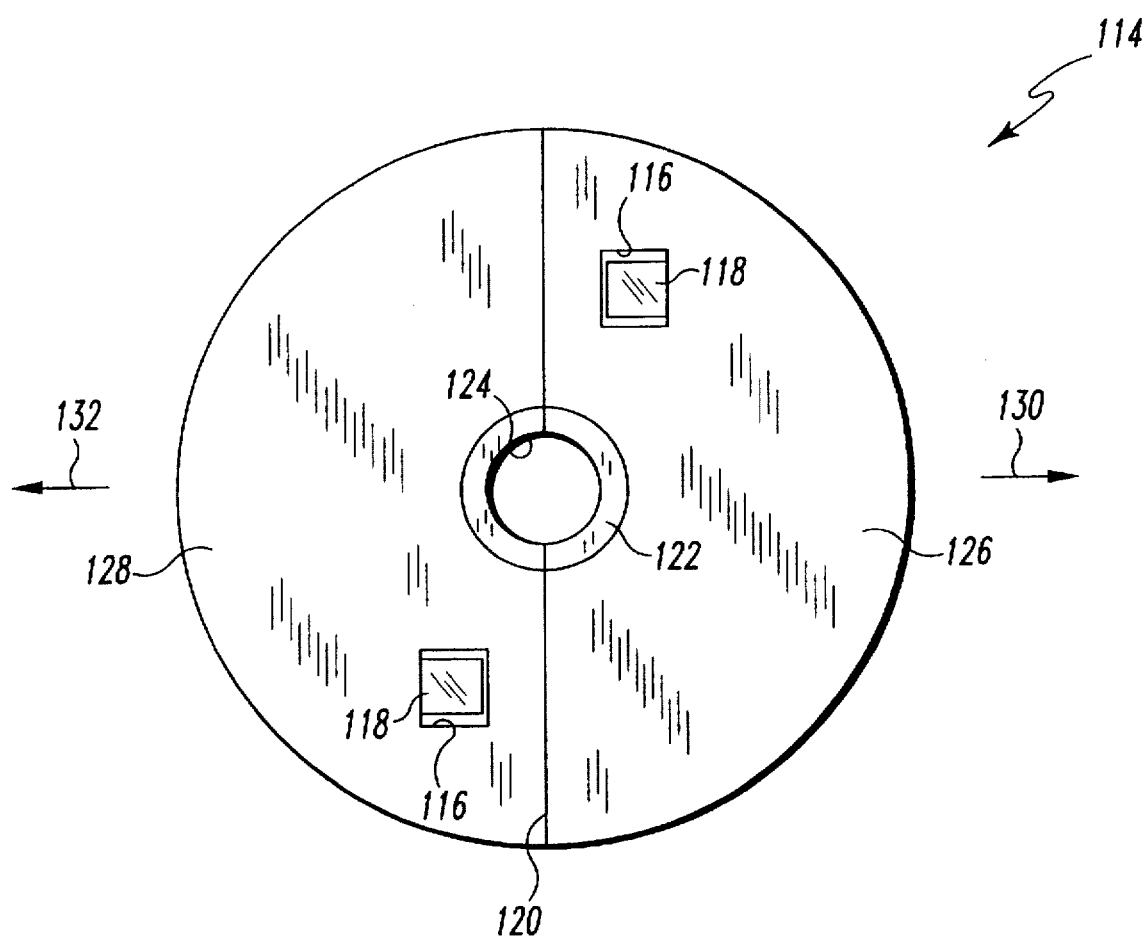
FIG. 11 is an elevational view of the lock member taken along line 11—11 of FIG. 10, with the body wall and the rest of the medical apparatus shown removed for clarity of description.

FIG. 11 is an elevational view of the lock member 114 taken along the line 11—11 of FIG. 10, with the body wall and the rest of the medical apparatus 100 shown removed for clarity of description. The lock member 114 is divided by a seam 120 into a first portion 128 and a second portion 126. Lock member 114 includes a fastening mechanism (which will be discussed in greater detail below) for fastening the first portion 128 to the second portion 126. The lock member also includes a positioning element 122 which defines an orifice 124 for accepting sleeve 106. The first portion 128 and the second portion 126 cooperate with each other so as to securely grasp the sleeve 106 therebetween. Lock member 114 can be made from any plastic material which is conventionally used in the medical device arts.

First portion 128 and second portion 126 can be separated by actuating the fastening mechanism (which will be discussed in detail below) and moving first portion 128 and second portion 126 in the direction of arrows 132 and 130, respectively. Separation of lock member 114 facilitates the insertion and removal of sleeve 106 from orifice 124.

Figure 12:
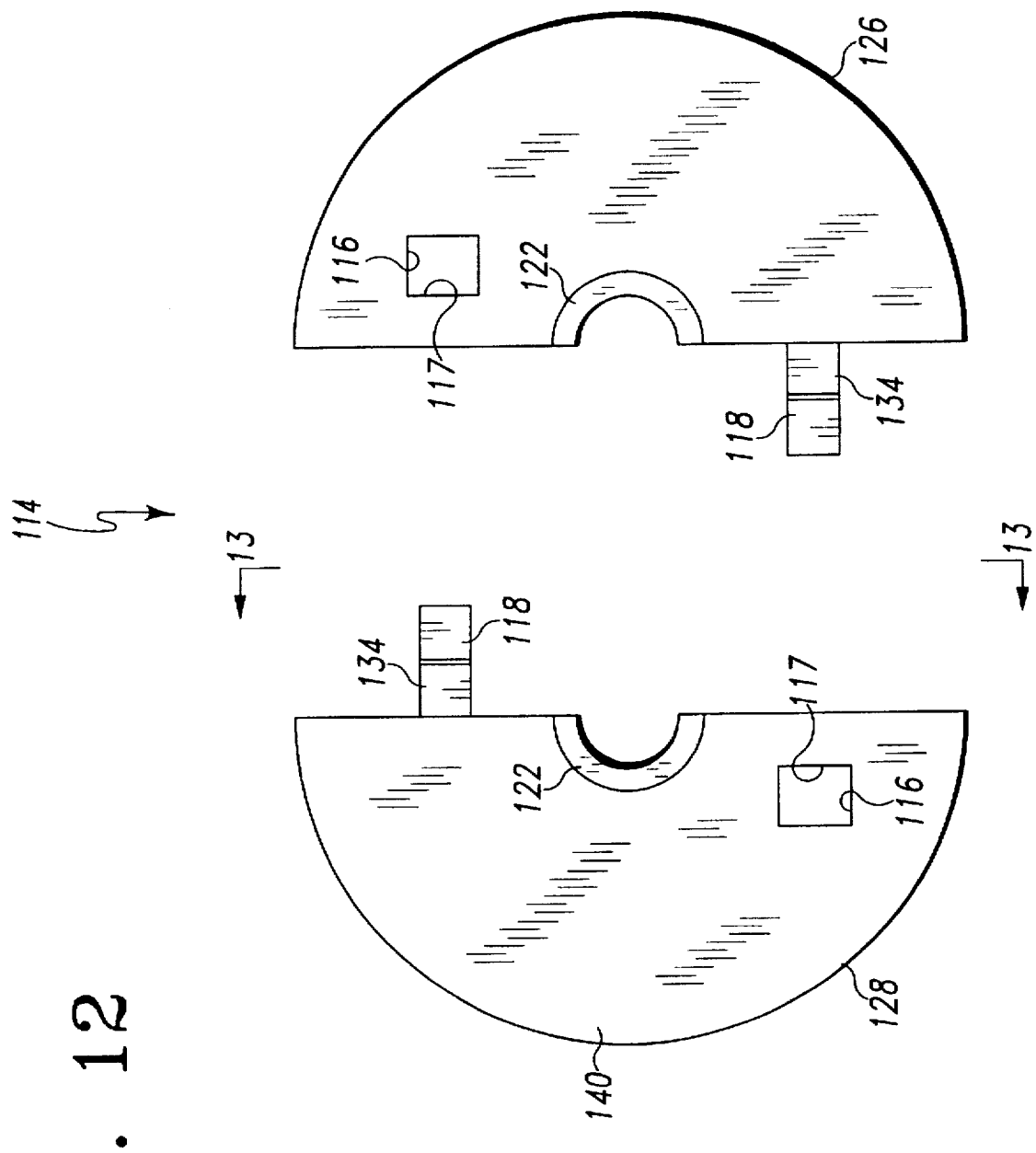
FIG. 12 is a side elevational view of the lock member of FIG. 11, with the first and second portions of the lock member shown separated.

As shown in FIGS. 11-14, the fastening mechanism includes a shaft 134 extending from an edge 142 of first portion 128 (It should be appreciated that, as illustrated in FIG. 12 second portion 126 has the same elements of the fastening mechanism as first portion 128. However, as discussed below, the fastening mechanism are arranged on second portion 126 to cooperate with those disposed on first portion 128.) The fastening mechanism also includes a clip 118 that obliquely extends from an end of shaft 134. Clip 118 is attached to shaft 134 using known manufacturing techniques that allows it to flex or bend around its point of attachment to shaft 134 in the directions indicated by arrow 141 (see FIG. 14).

Figure 13:
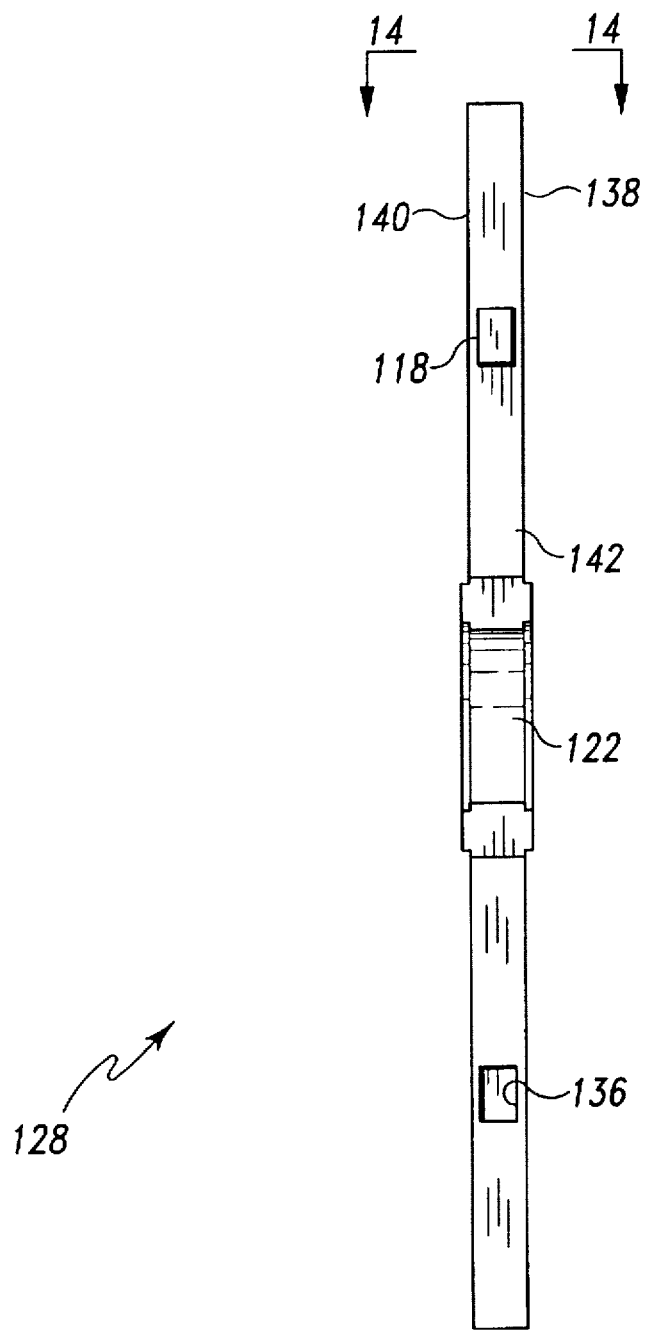
FIG. 13 is a side elevational view of the first portion of the lock member taken along line 13—13 of FIG. 12.
Figure 14:
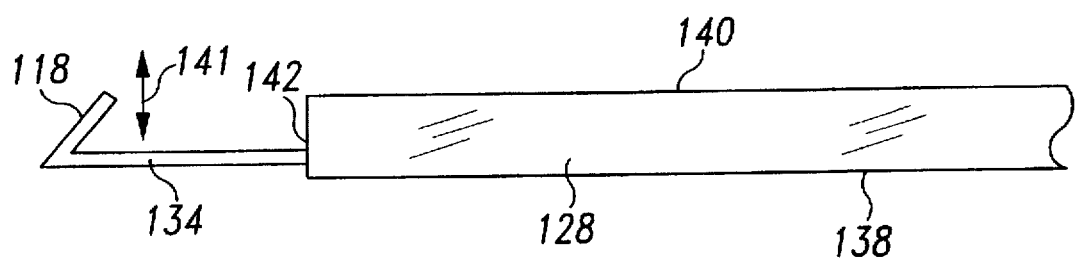
FIG. 14 is an enlarged fragmentary side elevational view of the first portion of the lock member taken along line 14—14 of FIG. 13.

As shown in FIGS. 12 and 13, the fastening mechanism also includes a channel 136 defined in edge 142, which is connected to an aperture 116 formed on second surface 140 of first portion 128. Channel 136 is adapted to receive clip 118 and shaft 134, and has the appropriate height dimension so that clip 118 must bend toward shaft 134 upon its entrance into channel 136. Medical apparatus 100 is used in the same manner as described above in reference to medical device 10 (see FIG. 1). However, once sealing members 104 are positioned in contact with interior surface 112, first portion 128 and second portion 126 of lock member 114 are positioned relative to each other so that the fastening mechanism elements can cooperate to join first portion 128 and second portion 126 along seam 120 (see FIG. 12). First portion 128 and second portion 126 are also positioned relative to sleeve 106 such that the sleeve 106 is positioned in orifice 124 and in contact with positioning element 122 when these portions are joined along seam 120. Once first portion 128 and second portion 126 are positioned in the above described manner, they are moved toward each other such that clip 118 and shaft 134 extending from second portion 126 enters channel 136 of first portion 128, and clip 118 and shaft 134 extending from first portion 128 enters the channel (not shown; identical to channel 136) located on the edge of second portion 126. As described above, as each clip 118 enters its respective channel 136 it is bent toward shaft 134 until entering its aperture 116. Once positioned in aperture 116 each clip snaps back to its unbent configuration where it engages wall 117 (see FIG. 12) thereby preventing the separation of the first portion 128 and second portion 126. The lock member can then be moved along the longitudinal axis of sleeve 106 until it contacts the exterior surface 111 of body cavity wall 108. As a result, wall 108 is trapped or "sandwiched" between lock member 114 and sealing member 104 thereby locking medical apparatus 100 into position with respect to wall 108. It should be understood that lock member 114 can also have any of the well known medical adhesives disposed thereon to facilitate its engagement with exterior surface 111. It should also be understood that a fastening mechanism utilizing velcro type fasteners can also be used in the present invention.

An important aspect of using lock member 114 in the above described manner is that the sealing members 104 remain in contact with interior surface 112 during the manipulations of medical apparatus 100 required by a medical procedure. By keeping sealing members 104 in contact with interior surface 112 fluid communication between an area inside of the body cavity and an area outside of the body cavity through opening 110 is prevented. Thus, the port site wound is protected from being exposed to potentially harmful substances including exfoliated cancer cells and/or infectious agents.

Another advantage of using lock member 114 is that it helps maintain a substantially gas tight seal between the interior and exterior of a body cavity, which ensures that no unexpected loss of a pneumoperitoneum will occur during a medical procedure. This is especially true when an adhesive is used to attach lock member 114 to exterior surface 111. It should be appreciated that preventing an uncontrolled loss of the pneumoperitoneum is important since such a loss can complicate the medical procedure being performed, and increase the potential that the port site wound will be contaminated with tumor cells or infectious microbes.

The use of lock member 114 may also eliminate the need for anyone to hold medical apparatus 100 in the appropriate position during surgery, thereby freeing them to perform other tasks. This is true since the first portion 128 and the second portion 126 cooperate with each other to securely grasp the sleeve 106 therebetween.

Once the medical procedure is completed, lock member 114 can be removed by depressing clip 118 (for example with a finger) toward shaft 134, (see FIG. 14) such that clip 118 can be inserted into channel 136, and moving first portion 128 and second portion 126 in the direction of arrows 132 and 130, respectively (see FIG. 11). Medical apparatus 100 can then be removed from the opening 110 as described above in reference to medical apparatus 10.

Figure 15:
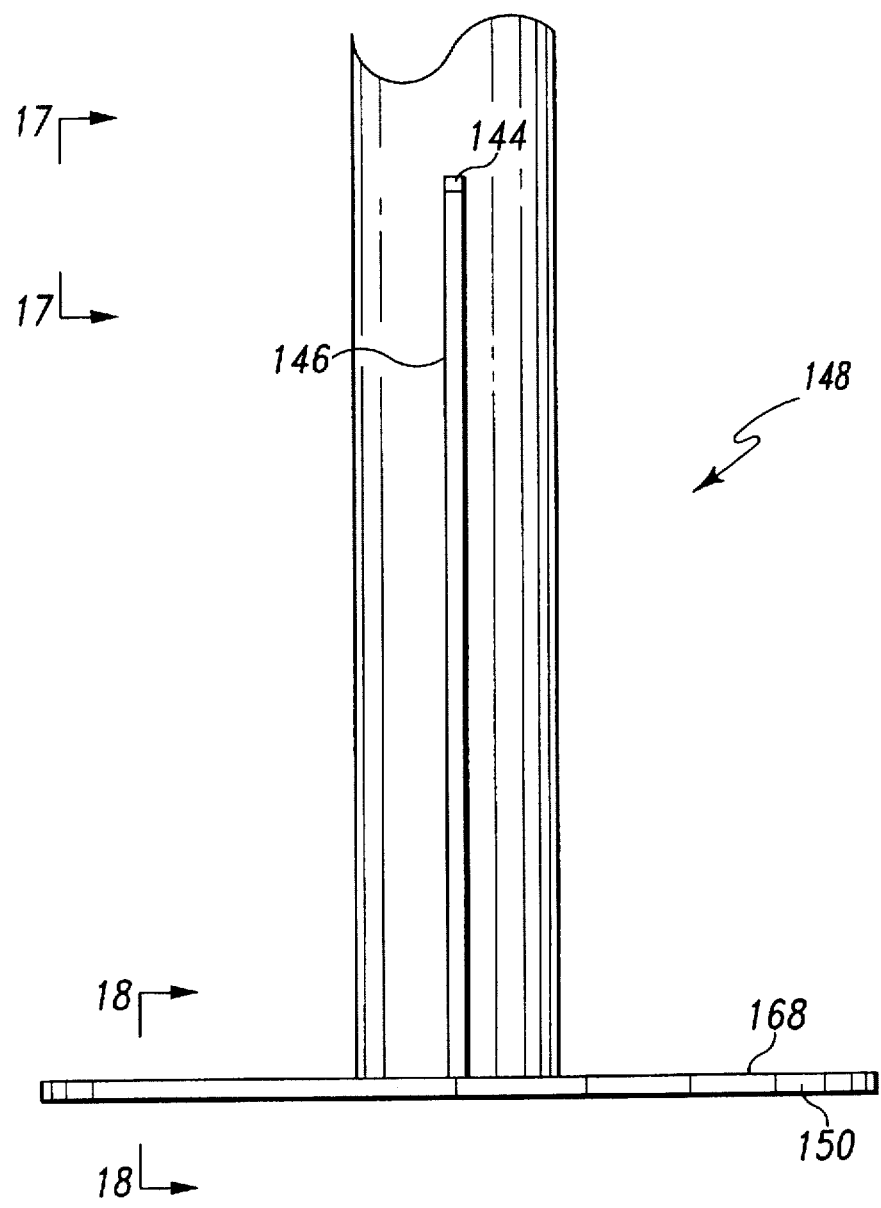
FIG. 15 is a side elevational view of another sleeve which incorporates the features of the present invention.
Figure 16:
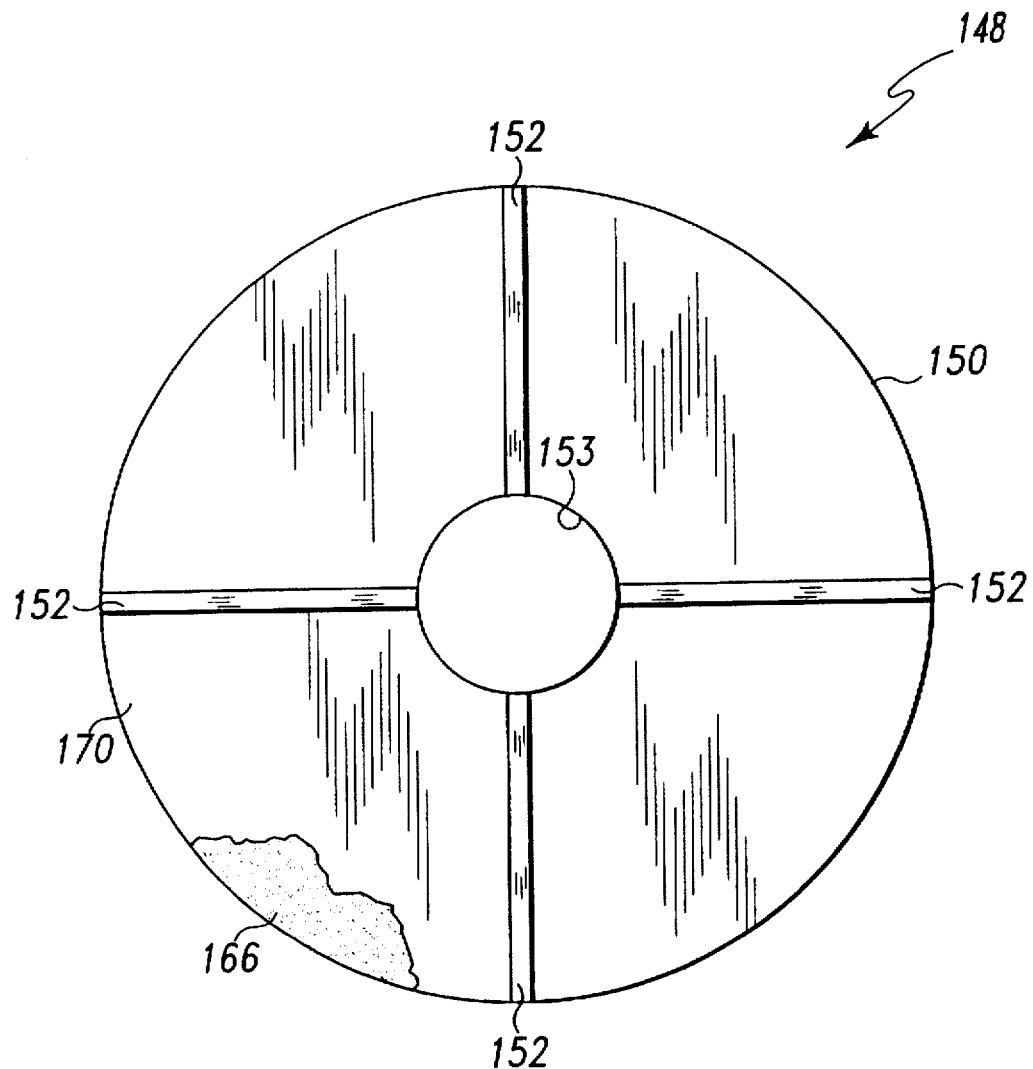
FIG. 16 is a side elevational view of the sealing member of the sleeve taken along line 16—16 of FIG. 15 with a biologically active compound disposed thereon (Note: that the biologically active compound is shown disposed on only a portion of the sealing member for clarity of description)
Figure 17:
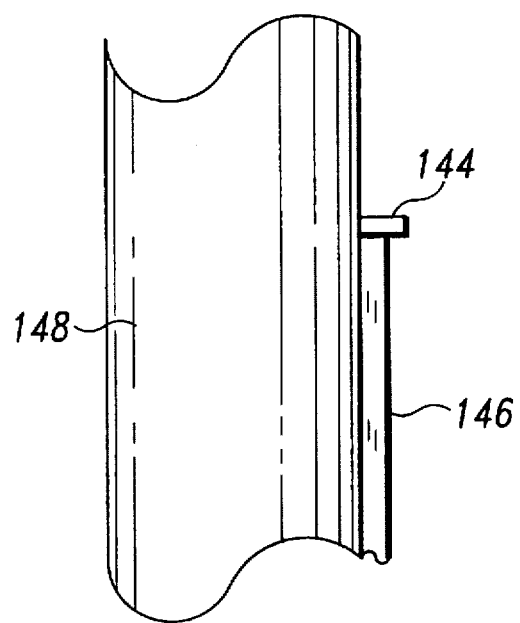
FIG. 17 is a fragmentary side elevational view of the sleeve taken along line 17—17 of FIG. 15.

Now referring to FIGS. 15–17, there is shown a sleeve 148 similar to sleeve 18 shown in FIG. 1 or sleeve 106 shown in FIG. 10. Sleeve 148 can be substituted for sleeve, 18 or sleeve 106 in medical apparatus 10 or 100, respectively. Moreover, sleeve 148 is used in a similar fashion as described for sleeve 18 or sleeve 106. However, as discussed in greater detail below, sleeve 148 includes a single sealing member 150 that defines a flexible gas impervious bag having a void 157 therein (see FIG. 18). One flexible gas impervious bag which may be used with some modification is disclosed in U.S. Pat. No. 3,762,404 issued to Sakita which is herin incorporated by reference. In particular, the void 157 contains a charge of small particles or beads 156 which consolidate or interengage into a rigid structure when the void 157 is evacuated. As shown in FIG. 16, the sleeve 148 has a passageway 153 extending therethrough adapted to accept a trocar assembly (not shown) which includes a cannula and a trocar. Sleeve 148 also has a number of support members 152 extending from a distal end of sleeve 148 (see FIG. 16) which engage sealing member 150. Support members 152 are formed such that when no force is applied to them they spontaneously assume the second orientation which is in a substantially orthogonal relationship with passageway 153 (see FIG. 16) thereby lifting and supporting the engaged sealing member 150 in its second orientation (see FIGS. 15 and 16). Moreover, support members 152 are flexibly attached to the distal end of sleeve 148 such that when force is applied (i.e. the force applied by sliding a guide member over support members 152 and sealing member 150) the support members 152 and the sealing member 150 assume their first orientation (i.e. positioned in a substantially parallel relationship with passageway 153).

As shown in FIGS. 15 and 17, sleeve 148 also includes a valve 144 and a vacuum line 146 in fluid communication with void 157. Valve 144 can have a well known female Luer-lock connector for attaching a vacuum hose (not shown) thereto. Moreover, valve 144 can be any of a number of well known valves capable of maintaining and then releasing a vacuum, as long as the size of the valve does not interfere with the operation of the medical apparatus into which sleeve 148 is incorporated. For example valve 144 can be a trumpet valve or a conventional two or three way stop cock valve.

Figure 18:
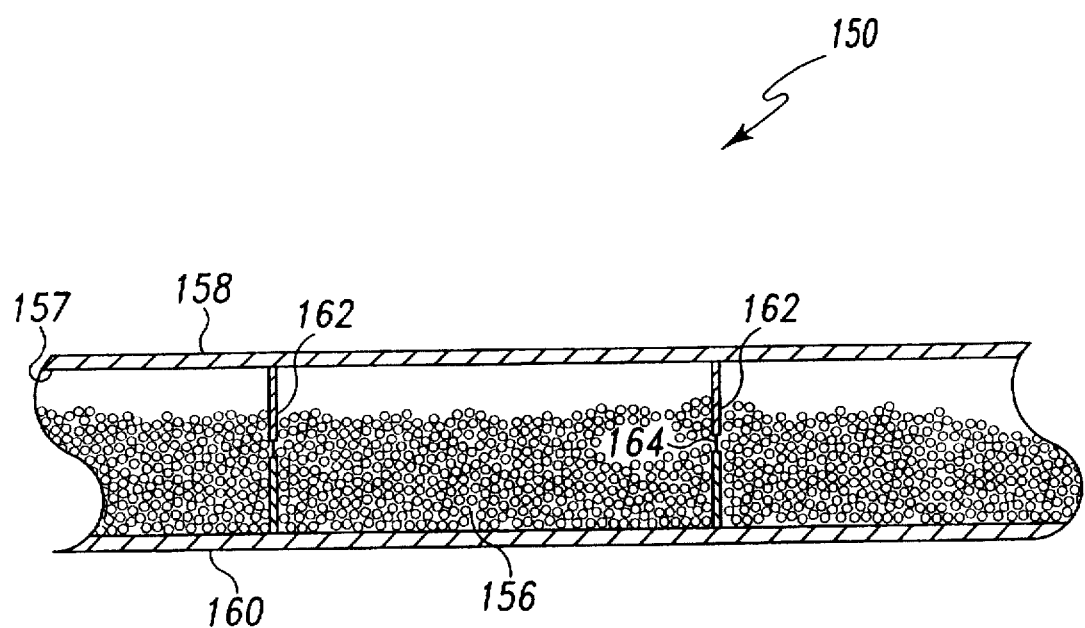
FIG. 18 is an enlarged fragmentary cross sectional view of the sealing member taken along line 18—18 of FIG. 15.

As illustrated in FIG. 18, the bag structure defined by sealing member 150 includes a first wall 158 and a second wall 160 with interior void 157 therebetween. The bag structure also includes a number of partitions 162 secured to and extending between first wall 158 and second wall 160 that divide interior void 157 into a number of compartments. These partitions 162 confine a portion of the charge of beads 156 into their respective compartment. It should be appreciated that having the beads 156 divided and confined into a number of compartments prevents the beads from being redistributed by gravity as sealing member 150 is moved between its first and second orientations, as well as, any movement which the beads are subjected to prior to evacuation of void 157. Each partition 162 has a screen 164 mounted therein which is adapted to allow the flow of a fluid therethrough but prevents a flow of beads from one compartment to another. Thus all the compartments are in fluid communication with one another and only one valve 144 and one vacuum line 146 are required to evacuate interior void 157.

The beads 156 occupying interior void 157 must be sufficiently rigid to withstand the stresses that result when they interengage upon evacuation of void 157. Beads 156 must also have a high mechanical strength so that void 157 can be repeatedly evacuated without the accompanying attrition or fracture of the beads 156. Beads 156 should also be elastically deformable such that when void 157 is evacuated they can move freely into close interengagement to form a stable, rigid structure.

Beads of expanded plastic material, such as polystyrene and polyvinyl chloride are preferred because of their high mechanical strength, elastic deformability and low specific gravity. The expression "specific gravity" is intended to mean a true specific gravity. Thus, when such beads are made hollow the specific gravity of the beads is represented by its weight divided by its total volume including the hollow space therein. The specific gravity of the beads used in the present invention should be in the range of from about 0.1 to about 0.6. Such values are readily attainable with foamed synthetic resins, although other material can be used for beads 156 when they have a low specific gravity in the range specified above and satisfy the mechanical strength and elastic deformability requirements.

The beads used in the present invention can be from about 0.5 to about 2 millimeters in diameter. Moreover, beads which are uniform in size and shape can be used, but a mixture of substantial portions of beads of at least two materially different sizes within the indicated range can also be used.

Any appropriate vacuum source (not shown) can be used to evacuate void 157. Such a vacuum source can be manually operated or power driven. Examples of vacuum sources which can be used in the present invention include a wall suction apparatus, aspirator pumps, or any other convenient operating vacuum source.

A medical apparatus incorporating sleeve 148 is used in a similar manner as described above in reference to medical device 10 and medical device 100. However, once sealing member 150 is positioned in contact with an interior surface of a body cavity wall, an end of a vacuum hose (not shown) is attached to valve 144 with the other end being attached to a vacuum source (not shown). A vacuum is pulled through valve 144 and vacuum line 146 thereby evacuating each compartment of interior void 157. It should be understood that since each partition 162 has a screen 164 therein, they will be in fluid communication with one another, therefore only one valve 144 and vacuum line 146 is required to evacuate interior void 157. As the vacuum is created inside interior void 157 the outside pressure present within the body cavity (e.g. an insufflated peritoneum) forces the beads 156 together into close interengagement so they cannot move. This interengagement of beads 156 upon evacuation of interior void 157 causes beads 156 to form a stable rigid structure, thereby converting seating member 150 from its pre-evacuation state of being a soft, pliable, deformable, flaccid structure (i.e. bean bag like) to its post-evacuation state of a stable rigid structure. When sealing member 150 is in its post-evacuation state, and in contact with an interior surface of a body cavity wall it effectively prevents fluid communication between an area inside of the body cavity and an area outside of the body cavity through a space defined between an opening in a wall of the body cavity and sleeve 148.

Once the medical procedure is completed, the vacuum is released and gas re-enters interior void 157 thereby disrupting the interengagement of beads 156. As a result sealing member 150 returns to its soft, pliable pre-evacuation state whereupon support member 152 (and therefore sealing member 150) are forced to assume their first orientation in the same manner as described above in reference to medical apparatus 10. The medical apparatus incorporating sleeve 148 is then withdrawn from the opening created in the body cavity wall.

An important aspect of using sealing member 150 in the above described manner is that in its pre-evacuation state its soft pliable nature allows it to conform to any irregular or protruding structures encountered on the interior surface of the body cavity wall. Then upon evacuation, sealing member 150 forms a rigid structure surrounding the encountered structure thus providing a fluid tight seal between the interior of the body cavity and the port site wound.

The present invention also includes a number of sealing members having a biologically active compound disposed thereon, such as an antibiotic, a cytotoxic agent or a compound which effectively inhibits tumor cell adherence to a membrane. As illustrated in FIG. 16, a biologically active compound 166 can be disposed on the side of sealing member 150 which does not engage the interior surface of the body cavity wall, referred to herein as non-contacting surface 170. However, it should be understood that biologically active compound 166 can also be disposed upon a contacting surface 168 (see FIG. 15) of sealing member 150 or on both of these surfaces. Moreover, it should be appreciated that biologically active compound 166 can be disposed upon sleeve 148 so that when it is positioned within a body cavity, biologically active compound 166 is in direct contact with opening 110. It should also be understood that biologically active compound 166 can also be disposed upon guide member 103. By doing so, the action of sliding guide member 103 into opening 110 will bring the same into contact with biologically active compound 166.

If necessary, in order to keep biologically active compound 166 from falling or sliding off sealing member 150 due to gravity as it is being positioned between the first and second orientation, biologically active compound 166 can contain a suitable pharmaceutically acceptable carrier. A pharmaceutically acceptable carrier will also aid in retaining all, or a portion of, the biologically active compound 166 on sealing member 150 as it is being advanced through an opening in a body cavity wall. Such pharmaceutically acceptable carriers include known excipients and auxiliaries which facilitate the processing of biologically active compound 166 into a preparation which has the appropriate, consistency to be disposed on sealing member 150.

Suitable excipients which may be used to prepare a pharmaceutically acceptable carrier, such as a paste, a viscous solution or a powder include fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Additionally, silica, talc, stearic acid or salts thereof such as magnesium stearate or calcium stearate, and/or polyethylene glycol can be used.

In addition, a suspension of biologically active compound 166 may be disposed on sealing member 150. Suitable vehicles for such suspensions include sesame oil or synthetic fatty acid esters, for example, ethyl oleate or triglycerides.

Such suspensions can include substances which increase the viscosity of the suspension including, for example, sodium carboxymethyl cellulose, sorbitol and/or a dextran.

The exact formulation of a pharmaceutically acceptable carrier will depend upon the particular nature of biologically active compound 166 to be disposed upon sealing member 150. It should also be understood that biologically active compound 166 can also be disposed upon the sleeve, such as sleeve 106, and the guide member, such as guide member 103. Moreover, the amount of biologically active compound 166 to dispose on sealing member 150 will depend upon the age, sex, weight, condition of the recipient, kind of concurrent treatment, if any, frequency of treatment and the nature of the effect desired. However, the amount of biologically active compound 166 to dispose on sealing member 150 is large enough to produce the desired effect but not so large as to cause adverse side effects, such as unwanted cross reactions, anaphylactic reactions and the like. Counterindication, if any, immune tolerance and other variables will also affect the proper amount to be disposed on sealing member 150. The exact formulation of a pharmaceutically acceptable carrier and the amount of biologically active compound 166 contained therein (and therefore the amount disposed on sealing member 150) is easily determinable by one of ordinary skill in the art from only routine experimentation and by applying well know principles of therapeutics as set forth, for example, in Gilman, Alfred G. et al., eds., *The Pharmacological Basis of Therapeutics*, 6$^{th}$ Edition, Macmillan Publishing Co., Inc. New York, N.Y. (1980) which is herein incorporated by reference. Preferably, such preparations will contain about 0.001 to about 99 percent biologically active compound 166 together with the pharmaceutically acceptable carrier.

A large number of antimicrobial agents (antibiotics) or antiseptics are contemplated for use as biologically active compound 166 in the present invention. Preferably, where possible, the antibiotic should be active against both Gram-positive and Gram negative pathogens. The following are illustrative of the antibiotics and/or antiseptics which can be disposed on sealing member 150 to aid in the control, inhibition or prevention of infections of the port site wound: (i) metal salts, or like compounds with antibacterial metal ions, e.g. copper or silver, and optionally with additional nonmetallic ions of antibacterial properties; (ii) typical antibiotics, e.g. neomycin, soframycin, bacitracin, polymcin; (iii) antibacterials such as chlorhexidine and its salts; (iv) quaternary ammonium compounds, e.g. centrimide, domiphen bromide, and polymeric quaternaries; (v) iodophors such as povidone iodine, and polyvinylpyrrolido-neiodine (PVP-I); (vi) acridine compounds such as 9-aminoacridine, 3,6-diaminoacridine and 6,9-diamino-2-ethoxyacridine; and (vii) biguanidine compounds such as 1,6-di(4-chlorophenylbiguanido)hexane, diaminohexylbiguanide, 1,6-di(aminohexylbiguanido) hexane, and polyhexamethylenebiguanide. Additional suitable antibiotics include aminoglycoside antibiotics such as amikacin, butirosin, dideoxykanamycin B (DKP), fortimycin, gentamycin, kanamycin, lividomycin, neomycin, netilmicin, ribostamycin, sagamycins, seldomycins and their epimers, sisomicin, sorbistin, tobramycin, streptomycins, linkomycins such as clindamycin, lincomycin and rifamycins such as rifampicin and rifamycin. Antibiotics such as polymyxin B sulfate-neomycin sulfate, cleocin phosphate ® (available from the Upjohn Company, Kalamazoo, Mich.) and erythromycin ethylsuccinate are also contemplated.

Examples of suitable antiseptics include bromchlorophen, hexetidine, buclosamide, salicylic acid, cerium nitrate, chlorhexidine, 5-chloro-8-hydroxyquinoline, copper 8-hydroxyquinolate, acridine orange, undecenoic acid, undecoylium chloride and silver salts such as silver sulfadiazine, mafenide, nitrofurazole, cloflucarban, tribromasalan, taurolin and noxythiolin.

With respect to aiding in the control, inhibition or prevention of tumor cell adhesion and implantation and the subsequent metastasis in the port site wound, compounds which effectively block or inhibit tumor cell adhesion (please note that tumor cell adhesion is a step in the metastasis cascade), or destroy tumor cells before adhering to either the port site wound, or other sites, can be disposed on sealing member 150. Types of compounds which effectively block or inhibit tumor cell adherence include anticoagulants, fibrinolytic agents and compounds which alter the electrical charge of a membrane surface. For example, the surface charge altering and anticoagulant heparin can be disposed on sealing member 150. Additionally, any of several water-soluble high molecular weight glucose polymers (average molecular weight (MW) 75 kdal) otherwise known as dextrans, can also be disposed on sealing member 150 to alter the surface electrical charge of nearby membranes thereby blocking tumor cell adhesion. Preferably a dextran having an average MW of about 40 kdal is used to coat sealing member 150.

As stated above, tumor cell destroying compounds, hereinafter referred to as cytotoxic compounds, can also be disposed on sealing member 150, with or without an acceptable pharmaceutically acceptable carrier. These compounds include cisplatin, carboplatin, 5-fluorouracil, providoneiodine, tumor necrosis factor (TNF)-α, tauromustine, mitomycin C, camptothecin, bleomycin, indomethacin, N-methyl formamide, tamoxifen, sodiumhypochlorite, chlorhexidinecetrimide, adriamycin, methotrexate. Tumor cell destroying compounds also include antimetabolites such as cytarabine, azaribine, mercaptopurine, thioguanine; natural products such as vinblastine, vincristine, dactinomycin, daunorubicin, doxorubicin, bleomycin, mithramycin, mitomycin; and other miscellaneous agents such as cisplatin, hydroxyurea, procarbazine and mitotane. Alkylating agents such as mechlorethamine, nitrogen mustards, ethlenimine derivatives, alkyl sulfonates, nitrosoureas, and triazenes are also contemplated. Moreover, the compounds disclosed by Krakoff, Irwin H. in *Systemic Treatment of Cancer*, CA Cancer J. Clin., vol. 46, No. 3, pages 134–141 (May/June 1996), which is incorporated herein by reference, are contemplated for being disposed on sealing member 150.

In addition antiangiogenesis agents such as angiostatin are included in the group of cytotoxic compounds to be disposed on sealing member 150. Moreover, antibodies, including human monoclonal antibodies are included as cytotoxic compounds. Preferably, the human monoclonal antibody HuMab SK1 as described by Chang, Helena R. et al. in *Human Monoclonal Antibody SK1-Mediated Cytotoxicity Against Colon Cancer Cells*, Dis. Colon Rectum, vol. 36, No. 12, pages 1152–1157 (December 1993) which is incorporated herein by reference, is disposed on sealing member 150. Other monoclonal antibodies can also be disposed on sealing member 150, for example those produced from hybridomas having the accession numbers HB8573, HB8232 and HB8250 available from the American Type Culture Collection, located at 12301 Parklawn Drive, Rockville Md., 20852. Furthermore, interleukin 2 (IL-2), cytokines or lymphokines are also included in the group of cytotoxic compounds of the present invention. It should also be understood that a combination of any of the above compounds can be disposed on sealing member 150.

In order to apply biologically active compound 166 to sealing member 150, the sealing member 150 is positioned in the second orientation (as previously described). Then, the biologically active compound 166 is disposed on the sealing member 150. Thereafter, sealing member 150 is repositioned to assume its first orientation, and then inserted through the opening defined in the body cavity wall as previously described. Then, the sealing member 150 is repositioned to assume its second orientation and thereafter moved into contact with the interior surface of the body wall cavity. It should be understood that biologically active compound 166 can be disposed on the contacting surface 168, the non-contacting surface 170 (see FIG. 16) or on both of these surfaces.

As discussed above, depending upon the nature of biologically active compound 166 (i.e. its ability to remain disposed on sealing member 150 when placed in the second orientation and advanced through an opening in a body cavity wall), it may be mixed with a pharmaceutically acceptable carrier prior to being disposed on sealing member 150. For example, biologically active compound 166 is suspended or dissolved in a 1% aqueous (weight/volume) solution of carboxymethylcellulose (CMC) before being applied to sealing member 150 (prospective example). Such a CMC solution provides the necessary viscosity to keep biologically active compound 166 from sliding or rolling off sealing member 150 when it is in the first position and being advanced through an opening in a body cavity wall.

Once located in the body cavity and in contact with an interior surface thereof, biologically active compound 166 establishes a "pharmacological barrier" between the interior of the body cavity and the opening in the body cavity wall. This "pharmacological barrier" helps prevent tumor cell implantation in the port site wound and/or the contamination of the port site wound with viable infectious microbes.

Based upon the above description it will be understood by those skilled in the art that the present invention provides a medical apparatus for protecting a port site wound which adds only a minimal amount of bulk to the diameter of a trocar assembly. Moreover, it will be understood by those skilled in the art that the medical apparatus of the present invention can be retrofit to existing trocar assembly technology. Furthermore, the medical apparatus of the present invention allows minimally invasive surgical techniques, such as laparoscopic surgery, to be safely applied to cancer surgery.

While the invention has been illustrated and described in detail in the drawings and foregoing description, such illustration and description is to be considered as exemplary and not restrictive in character, it being understood that only the preferred embodiments have been shown and described and that all changes and modifications that come within the spirit of the invention are desired to be protected. For example, while the mechanism described above for moving the sealing members from the first orientation to the second orientation has many benefits, other mechanisms may be used. One such mechanism may utilize pressure in the body cavity to force the sealing members against the interior surface thereof. Additional mechanisms which can be used to move the sealing members include the use of pistons attached to the sealing members, cords attached to the sealing members and a screw mechanism for actuating the sealing members. Furthermore, a system of tubes integrated in the sleeve can be used to deliver the biologically active compound to the sealing members via capillary action. Additionally, other materials are contemplated for use in making the sealing member. For example, foam, or other materials which are capable of altering their degree of pliability upon the application of a magnetic field or the use of electricity.

What is claimed is:

1. A medical apparatus, comprising:

a trocar assembly including a cannula and a trocar;

a sleeve having a number of sealing members extending therefrom and a passageway extending therethrough, said trocar assembly being positioned within said passageway of said sleeve; and a lock member which has hole defined therein, said sleeve extending through the hole, wherein said lock member comprises (1) a first lock portion, and (2) a second lock portion which is securable to said first lock portion, wherein said first lock edge of includes (1) a first shaft extending from an edge of said first lock portion, and (2) a clip extending from an end of said first shaft, wherein said second lock portion includes (1) a channel defined therein which receives the first shaft and the clip, and (2) an opening defined therein which is connected to the channel, and wherein the clip is exposed through the opening when the first lock portion is coupled to the second lock portion.

2. The medical apparatus of claim 1, wherein said lock member has an adhesive material disposed thereon.

3. A medical apparatus, comprising:

a trocar assembly including a cannula and a trocar;

a sleeve having a sealing member extending therefrom and a passageway extending therethrough, said trocar assembly being positioned within said passageway of said sleeve; and a lock member which has hole defined therein, said sleeve extending through the hole, wherein said sealing member defines a fluid impervious bag, wherein said bag has an interior void, and wherein a charge of elastically deformable beads are confined within said interior void.

4. A medical apparatus, comprising:

a trocar assembly including a cannula and a trocar;

a sleeve having a number of sealing members extending therefrom and a passageway extending therethrough, said trocar assembly being positioned within said passageway of said sleeve; and a lock member which has hole defined therein, said sleeve extending through the hole, wherein an antibiotic, a cytotoxic agent or a compound which inhibits tumor cell adherence to a membrane is disposed upon the number of sealing members.

5. A medical apparatus, comprising:

a trocar assembly including a cannula and a trocar;

a sleeve having a sealing member extending therefrom and a passageway extending therethrough, said trocar assembly being positioned within said passageway of said sleeve, and wherein (1) said sealing member defines a fluid impervious bag, (2) said bag has an interior void, and (3) a plurality of beads are confined within said interior void.

6. The medical apparatus of claim 5, wherein each of said plurality of beads are elastically deformable.

7. The medical apparatus of claim 5, further comprising a valve in fluid communication with the interior void of said bag.

8. The medical apparatus of claim 7, wherein said plurality of beads interengage with each other to form a rigid structure when fluid is evacuated from the interior void of said bag through said valve.

9. The medical apparatus of claim 5, wherein:

said bag includes a plurality of dividers located in the interior void of said bag so as to form a plurality of compartments, and said plurality of beads are subdivided into the plurality of compartments.

10. A medical apparatus, comprising:

a trocar assembly including a cannula and a trocar;

a sleeve having a number of sealing members extending therefrom and a passageway extending therethrough, said trocar assembly being positioned within said passageway of said sleeve; and an antibiotic, a cytotoxic agent, or a compound which inhibits tumor cell adherence to a membrane disposed upon said sealing members.

11. The medical apparatus of claim 10, wherein said antibiotic agent is polymyxin B sulfate-neomycin sulfate, cleocin phosphate, or erythromycin ethylsuccinate.

12. The medical apparatus of claim 10 wherein said cytotoxic agent is mechlorethamine, methotrexate, or 5-fluorouracil.

13. The medical apparatus of claim 10, wherein said compound which inhibits tumor cell adhesion to the membrane is heparin or a dextran, said dextran having a molecular weight of about 40 kdal.

14. The medical apparatus of claim 10 wherein said antibiotic, cytotoxic agent or the compound which inhibits tumor cell adherence to the membrane contains a carrier.

15. A medical procedure, comprising the steps of:

creating an opening in a wall of a body cavity;

advancing a medical apparatus through the opening and into the body cavity, the medical apparatus including (1) a sleeve having a number of sealing members connected thereto and a passageway extending therethrough, and (2) a trocar assembly positioned within the passageway of the sleeve, the trocar assembly including a cannula and a trocar;

positioning the sealing members to contact an interior surface of the body cavity;

providing a lock member having a hole extending therethrough;

positioning the lock member such that the sleeve extends through the hole; and applying the following material to the sealing members: an antibiotic, a cytotoxic agent or a compound which inhibits tumor cell adherence to a membrane.

16. The medical procedure of claim 15, wherein the hole is configured so that the sleeve is friction fit in the hole of the lock member.

17. The medical procedure of claim 15, further comprising the step of positioning the lock member in contact with an exterior surface of the body cavity.

18. A medical procedure, comprising the steps of:

creating an opening in a wall of a body cavity;

advancing a medical apparatus through the opening and into the body cavity, the medical apparatus including (1) a sleeve having a sealing member connected thereto and a passageway extending therethrough, and (2) a trocar assembly positioned within the passageway of the sleeve, the trocar assembly including a cannula and a trocar;

positioning the sealing member to contact an interior surface of the body cavity;

providing a lock member having a hole extending therethrough; and positioning the lock member such that the sleeve extends through the hole, wherein the sealing member defines a fluid impervious bag, wherein the bag has an interior void, wherein a charge of elastically deformable beads are confined within the interior void, and wherein the step of positioning the sealing member includes the step of evacuating air from the interior void of the bag.

* * * * *